(12) United States Patent
Baldwin

(10) Patent No.: US 7,787,159 B2
(45) Date of Patent: Aug. 31, 2010

(54) ACHIEVING CONVERGENT LIGHT RAYS EMITTED BY PLANAR ARRAY OF LIGHT SOURCES

(75) Inventor: Leo Baldwin, Beaverton, OR (US)

(73) Assignee: Electro Scientific Industries, Inc., Portland, OR (US)

(*) Notice: Subject to any disclaimer, the term of this patent is extended or adjusted under 35 U.S.C. 154(b) by 1089 days.

(21) Appl. No.: 11/482,539

(22) Filed: Jul. 7, 2006

(65) Prior Publication Data

US 2007/0014466 A1  Jan. 18, 2007

Related U.S. Application Data

(60) Provisional application No. 60/697,651, filed on Jul. 8, 2005.

(51) Int. Cl.
*H04N 1/04* (2006.01)
(52) U.S. Cl. ............... 358/482; 359/474; 359/483; 359/484
(58) Field of Classification Search ............ 358/482, 358/474, 483, 484, 475
See application file for complete search history.

(56) References Cited

U.S. PATENT DOCUMENTS

| 5,469,294 | A |   | 11/1995 | Wilt et al. |
|---|---|---|---|---|
| 5,737,122 | A | * | 4/1998 | Wilt et al. ............ 359/436 |
| 5,822,053 | A |   | 10/1998 | Thrailkill |
| 6,122,048 | A |   | 9/2000 | Cochran et al. |
| 6,222,624 | B1 |   | 4/2001 | Yonezawa |
| 6,385,507 | B1 |   | 5/2002 | Buijtels |
| 6,538,243 | B1 | * | 3/2003 | Bohn et al. ............ 250/208.1 |
| 6,580,813 | B1 |   | 6/2003 | Hermanns et al. |
| 6,870,949 | B2 | * | 3/2005 | Baldwin ............ 382/145 |
| 2002/0080236 | A1 |   | 6/2002 | Madsen et al. |
| 2002/0135757 | A1 |   | 9/2002 | Shires |
| 2002/0181231 | A1 |   | 12/2002 | Luk |
| 2004/0037089 | A1 |   | 2/2004 | Bushell et al. |
| 2004/0141175 | A1 |   | 7/2004 | Baldwin et al. |

OTHER PUBLICATIONS

Search Report and Written Opinion Concerning the Corresponding International Application No. PCT/US2006/026685.

* cited by examiner

*Primary Examiner*—Houshang Safaipour
(74) *Attorney, Agent, or Firm*—Stoel Rives LLP

(57) ABSTRACT

Systems and methods are provided for achieving convergent light rays emitted by a planar array of light sources. In one embodiment, an imaging device is provided for inspecting semiconductors or other objects. The imaging device includes one or more imaging lens for imaging light reflected from an object. The imaging device also includes a first light source attached to a planar circuit board and a second light source attached to the planar circuit board. The imaging device further includes a first Fresnel prism for directing light from the first light source toward the object from a first direction and a second Fresnel prism for directing light from the second light source toward the object from a second direction. In one embodiment, the imaging device also includes one or more optical elements for increasing or decreasing the divergence of the light.

18 Claims, 2 Drawing Sheets

ACHIEVING CONVERGENT LIGHT RAYS EMITTED BY PLANAR ARRAY OF LIGHT SOURCES

RELATED APPLICATION

This application claims the benefit under 35 U.S.C. §119(e) of U.S. Provisional Application No. 60/697,651, filed Jul. 8, 2005, which is hereby incorporated by reference herein in its entirety.

TECHNICAL FIELD

This disclosure relates to illuminating objects with convergent light rays.

BACKGROUND INFORMATION

The way in which an object reflects light can vary from perfectly diffuse, known in the art as Lambertian (after Lambert), to perfectly specular (after speculum, a mirror). If an object is substantially Lambertian in nature in that the surfaces reflect light with an efficiency which is essentially independent of angle, then the illumination of such an object is relatively simple. In such a case, the uniformity of an image of an object relies only upon the uniformity and intensity of the incident illumination. An example of a Lambertian object would be paper, which can be adequately illuminated by a single point-like source of light.

If an object is substantially specular and the desired illumination is bright field illumination, then the light source will be seen directly by the observer. This can be accomplished by placing a camera at an off angle which is the same as the off angle of a light source in so much as the angle of reflection on a specular object complements the angle of incidence. In such a case the source itself must have the characteristics of a Lambertian emitter and must encompass the projected field of view.

Between substantially diffuse reflecting Lambertian objects and substantially specular reflecting object there exists a very large class of objects for which the surfaces are neither substantially Lambertian nor substantially specular. For these objects, the amount of light reflected from a light source to the observer or sensing device depends both on the intensity of the incident illumination and the angle of incidence.

Designing a lighting system for imaging an object entails directing a light in a specific direction, generally toward the object being imaged. The usual way to accomplish this is to point or aim a light source in the direction of the object. This aiming can be quite involved. For example, U.S. Patent Application Publication No. 2004/0141175, filed as U.S. patent application Ser. No. 10/616,548 on Jul. 10, 2003 by Baldwin et al., presents an example of aiming light sources such as light emitting diodes (LEDs) from different directions to achieve uniform illumination of an object at a substantially constant angle of illumination regardless of the location of the object.

Darkfield ringlights are generally used to illuminate objects from a plurality of directions. A darkfield ringlight produced using state-of-the-art techniques includes LEDs incorporating a rudimentary condensing lens mounted to four, for example, individual circuit board segments such that the LEDs may be angled toward the object from different directions. Each circuit board segment is mounted at a suitable angle and positioned such that its energy is directed toward the object. The principal rays of the LEDs converge at a predetermined location. Although this arrangement provides adequate illumination, there are difficulties associated with its implementation. For example, it is expensive to produce, mount and interconnect four separate circuit board assemblies.

SUMMARY OF THE DISCLOSURE

Thus, it would be preferable to mount the light sources (e.g., LEDs) of a darkfield ringlight on a single circuit board to reduce parts count, cost of parts, assembly time, and assembly cost. It would also be preferable to increase reliability by virtue of fewer interconnects.

In one embodiment, an imaging device is provided for inspecting semiconductors or other objects. The imaging device includes one or more imaging lenses for imaging light reflected from an object and a planar circuit board. The imaging device also includes a first light source attached to the planar circuit board and a second light source attached to the planar circuit board. The imaging device includes a first Fresnel prism for directing light from the first light source toward the object from a first direction and a second Fresnel prism for directing light from the second light source toward the object from a second direction.

In one embodiment, a darkfield ringlight includes a first light source for emitting a first beam of light, a second light source for emitting a second beam of light substantially parallel to the first beam of light, and one or more optical elements for redirecting the first beam of light and the second beam of light such that the first beam of light and the second beam of light converge at a desired location.

In one embodiment, a method for illuminating an object includes emitting a first beam of light, emitting a second beam of light substantially parallel to the first beam of light, and redirecting the first beam and the second beam such that the beams converge at a selected location.

In one embodiment, a light source for a manufacturing inspection system includes means for redirecting two or more substantially parallel beams of light toward an object to be imaged, and means for changing the divergence of at least one of the beams of light.

Additional aspects and advantages will be apparent from the following detailed description of preferred embodiments, which proceeds with reference to the accompanying drawings.

DETAILED DESCRIPTION OF PREFERRED EMBODIMENTS

Figure 1:
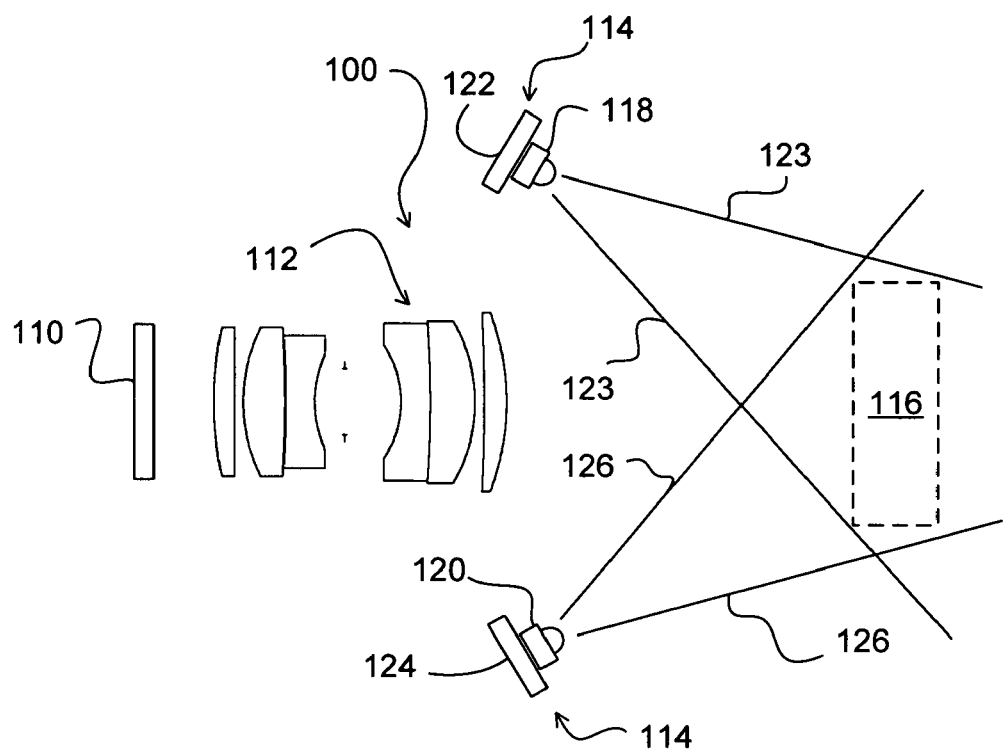
FIG. 1 is a schematic diagram of a conventional imaging device.

In one embodiment, light rays are emitted by a planar array of light sources and directed so as to illuminate an object under observation. Typically, although the present disclosure is not so limited, the planar array of light sources may be employed for the automated characterization and/or inspection of manufactured parts. These manufactured parts include semiconductors. Classes of semiconductors may have a nontrivial bi-directional reflectance distribution function thereby presenting varying illumination properties from Lambertian to specular. It is well understood that the time necessary to accurately inspect certain manufactured parts such as semiconductors is limited with any error reducing the efficiency of the overall production rate. An illumination device, according to one embodiment, reduces errors in inspection associated with illumination and thereby contributes to the overall efficiency of the manufacturing process.

Reference is now made to the figures in which like reference numerals refer to like elements. For clarity, the first digit of a reference numeral indicates the figure number in which the corresponding element is first used. In the following description, numerous specific details are provided for a thorough understanding of the embodiments disclosed herein. However, those skilled in the art will recognize that the embodiments described herein can be practiced without one or more of the specific details, or with other methods, components, or materials. Further, in some cases, well-known structures, materials, or operations are not shown or described in detail in order to avoid obscuring aspects of the embodiments. Furthermore, the described features, structures, or characteristics may be combined in any suitable manner in one or more embodiments.

FIG. 1 is a schematic diagram of a conventional imaging device 100. The imaging device 100 includes a sensing element 110, a lens arrangement 112, and a light source 114. The sensing element 110 may include, for example, a charge coupled device (CCD) or a complementary metal oxide semiconductor (CMOS) camera. The lens arrangement 112 is configured to provide to the sensing element 110 an image of an object 116. The sensing element 110 and lens arrangement 112 may be of any construction including conventional and non-conventional. For example, the lens arrangement 112 may be telecentric.

The light source 114 is positioned to illuminate the object 116 from two or more different directions (two shown). The light source 114 may be positioned such that each point on the object 116 is illuminated at an angle substantially the same as a nominal illumination angle. Providing lighting with the same angle of incidence across the object 116 improves the lighting for objects that are specular to any degree. The nominal illumination angle is the angle which most effectively illuminates the object 116. It is understood that the nominal illumination angle will vary depending upon the qualities of the object 116 being imaged.

The nominal illumination angle may be determined empirically to provide a preferred illumination effect; it may be determined by mathematical modeling of the object 116, the light source 114, and the sensing element 110; or it may be restricted to a particular nominal value by the available space for the imaging device 100. Empirical determination may involve trial and error over the object 116 to determine an optimum angle of illumination. An example of a mathematical approach would be a Monte Carlo ray tracing. A Monte Carlo ray tracing involves the use of a random variable package which creates Monte Carlo ray tracings. An example of a software package capable of such mathematical modeling is sold by Lambda Research Corporation of Littleton, Mass. under the name Trace Pro.

The light source 114 includes a first illumination device 118 and a second illumination device 120. The first illumination device 118 and the second illumination device 120 may each comprise, for example, a light emitting diode (LED). The LEDs may each include a condensing lens to concentrate light onto the object 116. An artisan will recognize that, alternatively, the first illumination device 118 and the second illumination device 120 may each comprise a one-dimensional or two-dimensional array of LEDs to provide increased brightness and/or uniform illumination of the object 116. As shown in FIG. 1, the light source 114 may be constructed to subtend the projected dimension and surround the object 116. To subtend the projected dimension of the object 116, it is understood that the light source 114 has a sufficient divergence. It is understood that the illumination device 114 can also be constructed so as not to subtend the projected dimension.

The first illumination device 118 is mounted to a first printed circuit board (PCB) 122. The first PCB 122 is positioned so as to direct light rays 123 from the first illumination device 118 toward the object 116 from a first direction. The second illumination device 120 is mounted to a second PCB 124. The second PCB 124 is positioned so as to direct light rays 126 from the second illumination device 120 toward the object 116 from a second direction. Thus, light rays 123, 126 from the first illumination device 118 and the second illumination device 120 converge on the object 116 to provide a desired darkfield lighting arrangement. An artisan will understand that the light source 114 may be of circular symmetry, two-fold symmetry, four-fold symmetry, or be of any other configuration which is suited to the object 116 and the available space.

As discussed above, using a segmented PCB such as the first PCB 122 and the second PCB 124, is more expensive than using a single PCB. Circuitry, such as an LED driver or a portion thereof, may need to be duplicated on the first PCB 122 and the second PCB 124. Further, it may be difficult to mount and interconnect the first PCB 122 and the second PCB 124. U.S. Patent Publication No. 2004/0141175 discloses using segmented PCBs or a flexible PCB formed into a cone, for example, to provide converging light rays from a plurality of different directions. However, both of these solutions may be more expensive and/or less reliable than a single rigid planar PCB.

Placing the first illumination device 118 and the second illumination device 120 on a single planar PCB (not shown in FIG. 1), according to one embodiment, requires that the respective light rays 123, 126 be redirected so as to converge on the object 116. A beam of light can be deviated by a prism through an angle in one dimension. However, conventional prisms positioned proximate the first illumination device 118 and the second illumination device 120 are too large for most applications. Thus, conventional prisms generally extend too far past the light source 114 for distances used between the light source 114 and the object 116. In one embodiment, the distance between the light source 114 and the object 116 is approximately 25 mm. In other embodiments, the distance between the light source 114 and the object 116 is in a range between approximately 20 mm and approximately 60 mm. An artisan will recognize that other ranges are possible. However, a minimum clearance distance should be maintained in front of the object 116 to allow room for a handling mechanism, such as a robotic arm with a fixture for picking up and placing the object 116.

As discussed in detail below, in one embodiment, a repeating array of miniature prisms is used to redirect light from a planar array of light sources so as to converge the light on the object 116. In one such embodiment, the repeating array of miniature prisms comprises a flattened prism referred to as a Fresnel prism because it resembles a Fresnel lens, but in one dimension. Thus, the Fresnel prism achieves the result of a much larger conventional prism in much the same way that a Fresnel lens is a flattened version of a conventional lens including a concentric array of annular facets.

Figure 2:
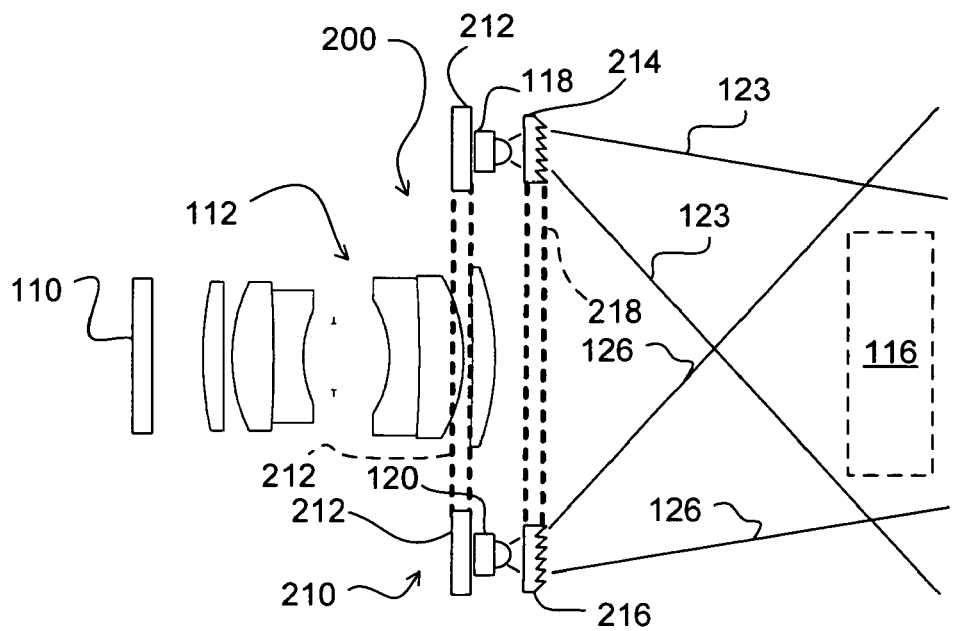
FIG. 2 is a schematic diagram of an imaging device for achieving convergent light rays according to one embodiment.

FIG. 2 is a schematic diagram of an imaging device 200 for achieving convergent light rays according to one embodiment. As discussed above, the imaging device 200 includes the sensing element 110 and the lens arrangement 112. However, the imaging device 200 includes a light source 210 having a planar array of illumination sources. In the example embodiment shown in FIG. 2, the light source 210 includes the first illumination device 118 and the second illumination device 120 mounted on a single, rigid PCB 212. For illustrative purposes, a portion of the PCB 212 is illustrated as a dashed line extending from the first illumination device 118 to the second illumination device 120. The PCB 212 is configured so as to not interfere with the lens arrangement 112. For example, in one embodiment, the PCB 212 includes an aperture that allows light reflected from the object 116 to be imaged by the lens arrangement 112.

As discussed above, the first illumination device 118 and the second illumination device 120 may each include a single LED or an array of LEDs. The first illumination device 118 and the second illumination device 120 are mounted on the PCB 212 so as to initially project light substantially perpendicular from a plane corresponding to the PCB 212. The light source 210 also includes a first Fresnel prism 214 positioned so as to redirect the light rays 123 from the first illumination device 118 onto the object 116 from the first direction, and a second Fresnel prism 216 positioned so as to redirect the light rays 126 from the second illumination device 120 onto the object 116 from the second direction. As discussed above, the angles for the first direction and the second direction may be selected so as to achieve a desired darklighting effect.

In one embodiment, the first Fresnel prism 214 and the second Fresnel prism 216 comprise injection molded Fresnel prisms. If the prisms 214, 216 have many small facets, the prisms are thin and flexible. However, if fewer facets are used, each facet is relatively larger and combine with a support structure such that prisms 214, 216 are rigid and several millimeters thick. In one embodiment, the Fresnel prisms 214, 216 have a thickness of approximately 1.2 mm with facets comprising approximately half of the thickness. Such a structure is sufficiently thick to be rigid and self supporting when mounted by the corners. In other embodiments, the Fresnel prisms 214, 216 have a thickness in a range between approximately 0.1 mm and approximately 5 mm.

In one embodiment, the Fresnel prisms 214, 216 include clear, flexible polyvinyl chloride plastic sheets that are modified to create prismatic effects. The sheets comprise a series of small prisms, aligned with their apex lines substantially parallel on a thin platform of plastic. An artisan will recognize from the disclosure herein that the first Fresnel prism 214 and the second Fresnel prism 216 may comprise a single Fresnel prism and/or may be formed on a single plastic sheet, as represented in FIG. 2 by dashed line 218.

The Fresnel prisms 214, 216 deflect the light rays 123, 126 to achieve the same desired convergence as though the first illumination device 118 and the second illumination device 120 were not planar but tilted toward the object 116. Using the Fresnel prisms 214, 216 allows improved or optimal lighting performance to be achieved with the first illumination device 118 and the second illumination device 120 mounted on the planar PCB 212. Thus, the number of electrical components, assembly time, and costs are reduced as compared to using multiple PCBs. Further, an increased reliability is achieved by virtue of fewer interconnects between multiple PCBs.

In one embodiment, the first illumination device 118 and the second illumination device 120 each have a divergence selected so as to substantially subtend the object 116. However, changes in the divergence, changes in the working distance between the light source 114 and the object 116, and/or changes in the size of the object 116 may result in a reduction in lighting quality. For example, too much divergence may result in light being wasted, and too little divergence may result in a dark periphery. Thus, in one embodiment, in addition to bending or redirecting light from the first illumination device 118 and the second illumination device 120, the divergence of the light is adjusted to properly illuminate the object 116.

Figure 3:
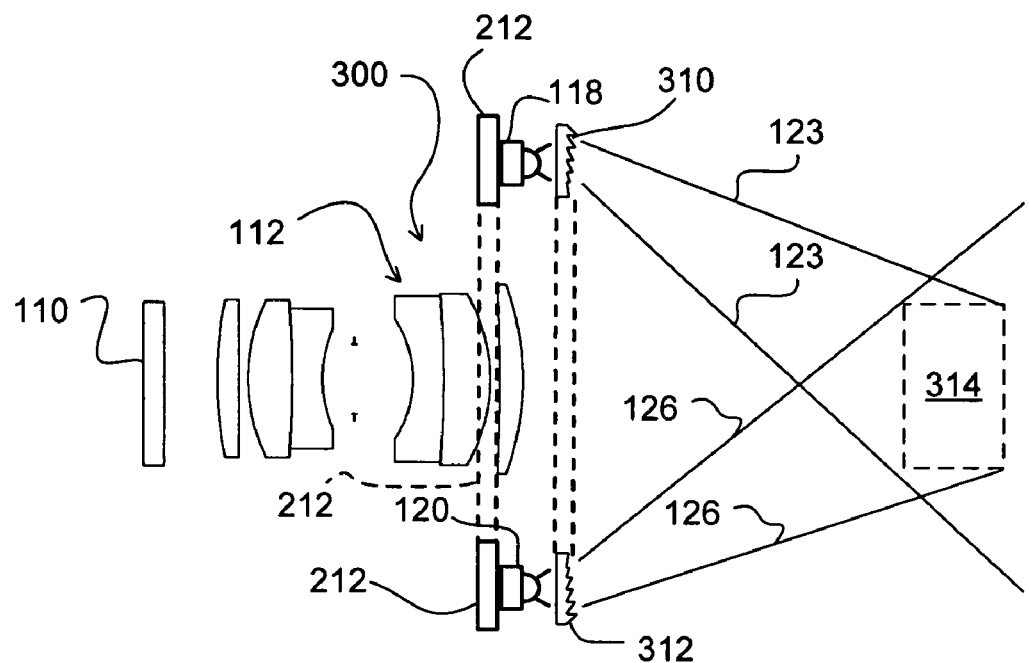
FIG. 3 is a schematic diagram of an imaging device for decreasing divergence of converging light rays according to one embodiment.

For example, FIG. 3 is a schematic diagram of an imaging device 300 for decreasing divergence of converging light rays according to one embodiment. The imaging device 300 includes a first optical element 310 configured to redirect and decrease the divergence of light emitted from the first illumination device 118. The imaging device 300 also includes a second optical element 312 configured to redirect and decrease the divergence of light emitted from the second illumination device 120. An artisan will recognize from the disclosure herein that the first optical element 310 and the second optical element 312 may comprise a single unit rather than two separate elements.

In one embodiment, the first optical element 310 and the second optical element 312 comprise a combination of a positive Fresnel lens and a Fresnel prism having a set of facets of varying angles. Thus, the first optical element 310 and the second optical element 312 deflect light from the first illumination device 118 and the second illumination device 120, respectively, towards an object 314.

In this example, the object 314 is shorter than the object 116 shown in FIGS. 1 and 2. Thus, the first optical element 310 and the second optical element 312 respectively decrease the divergence of the light emitted from the first illumination device 118 and the second illumination device 120 so that excessive light is not wasted. Other embodiments for decreasing the divergence include, for example, positioning a positive lens or positive Fresnel lens in front of the Fresnel prisms 214, 216 shown in FIG. 2. An artisan will recognize from the disclosure herein other embodiments for decreasing the divergence.

Figure 4:
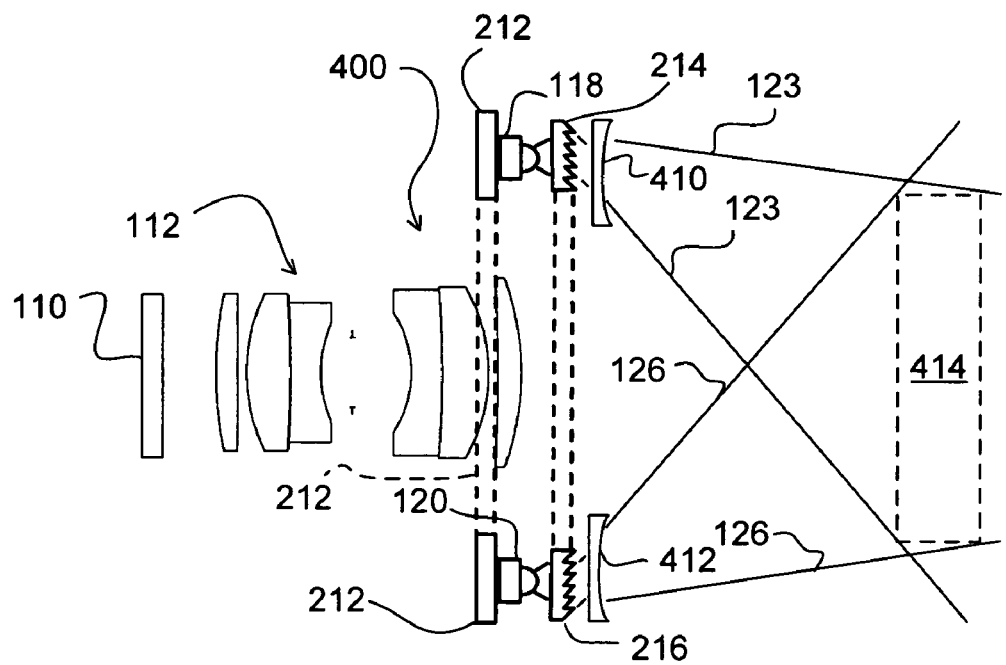
FIG. 4 is a schematic diagram of an imaging device for increasing divergence of converging light rays according to one embodiment.

FIG. 4 is a schematic diagram of an imaging device 400 for increasing divergence of converging light rays according to one embodiment. The imaging device 400 includes a first negative lens 410 positioned relative to the first Fresnel prism 214 so as to add divergence to the light emitted from the first illumination device 118. The imaging device 400 also includes a second negative lens 412 positioned relative to the second Fresnel prism 216 so as to add divergence to the light emitted from the second illumination device 120. An artisan will recognize from the disclosure herein that the first negative lens 410 and the second negative lens 412 may comprise a single lens rather than two separate lenses.

In the example shown in FIG. 4, an object 414 is longer than the object 116 shown in FIGS. 1 and 2. Thus, after the first Fresnel lens 214 and the second Fresnel lens 216 direct the light beams toward the object 414, the first negative lens 410 and the second negative lens 412 respectively add divergence to the beams so that the light covers the entire object 414. To add divergence to the emitted beams, according to another embodiment, the first negative lens 410 and the second negative lens 412 are replaced with one or more diffusers. In another embodiment, divergence is added to the emitted beams using a negative Fresnel lens combined with a Fresnel prism. In another embodiment, a diffuser is combined with a Fresnel prism. For example, a plastic sheet supporting the Fresnel prism 214 may have a surface suitable for light diffusion molded into the side opposite the Fresnel prism's facets. An artisan will recognize from the disclosure herein other embodiments for adding divergence to the light beams.

It will be obvious to those having skill in the art that many changes may be made to the details of the above-described embodiments without departing from the underlying principles of the invention. The scope of the present invention should, therefore, be determined only by the following claims.

The invention claimed is:

1. An imaging device for inspecting semiconductors, the imaging device comprising:
    one or more imaging lens for imaging light reflected from an object;
    a planar circuit board;
    a first light source attached to the planar circuit board;
    a second light source attached to the planar circuit board;
    a first Fresnel prism for directing light from the first light source toward the object from a first direction;
    a second Fresnel prism for directing light from the second light source toward the object from a second direction; and
    an optical element for decreasing divergence in the light directed by at least one of the first Fresnel prism and the second Fresnel prism.

2. The imaging device of claim 1, further comprising a sensing element for receiving an image of the object from the one or more imaging lens.

3. The imaging device of claim 1, wherein the optical element is selected from the group consisting of a positive lens and a positive Fresnel lens.

4. The imaging device of claim 1, wherein at least one of the first light source and the second light source comprises a light emitting diode.

5. The imaging device of claim 1, wherein at least one of the first light source and the second light source comprises an array of light emitting diodes.

6. A darkfield ringlight comprising:
    a first light source for emitting a first beam of light;
    a second light source for emitting a second beam of light substantially parallel to the first beam of light; and
    one or more optical elements for redirecting the first beam of light and the second beam of light such that the first beam of light and the second beam of light converge at a desired location,
    wherein the one or more optical elements is configured to reduce divergence in at least one of the first beam and the second beam.

7. The darkfield ringlight of claim 6, wherein at least one of the first light source and the second light source comprises one or more light emitting diodes.

8. The darkfield ringlight of claim 6, wherein the one or more optical elements comprises a Fresnel prism.

9. The darkfield ringlight of claim 6, wherein the one or more optical elements further comprises an element selected from the group consisting of a positive lens and a positive Fresnel lens.

10. The darkfield ringlight of claim 6, wherein the one or more optical elements comprises a combined Fresnel lens and Fresnel prism having facets of varying angles.

11. The darkfield ringlight of claim 6, further comprising a circuit board, the first light source and the second light source mechanically coupled to a planar surface of the circuit board.

12. A method for illuminating an object, the method comprising:
    emitting a first beam of light;
    emitting a second beam of light substantially parallel to the first beam of light;
    redirecting the first beam and the second beam such that the beams converge at a selected location; and
    decreasing the divergence of at least one of the first beam and the second beam.

13. A darkfield ringlight comprising:
    a first light source for emitting a first beam of light;
    a second light source for emitting a second beam of light substantially parallel to the first beam of light; and
    one or more optical elements for redirecting the first beam of light and the second beam of light such that the first beam of light and the second beam of light converge at a desired location,
    wherein the one or more optical elements is configured to increase divergence in at least one of the first beam and the second beam.

14. The darkfield ringlight of claim 13, wherein at least one of the first light source and the second light source comprises one or more light emitting diodes.

15. The darkfield ringlight of claim 13, wherein the one or more optical elements comprises a Fresnel prism.

16. The darkfield ringlight of claim 13, wherein the one or more optical elements further comprises an element selected from the group consisting of a diffuser, a negative lens, and a negative Fresnel lens.

17. The darkfield ringlight of claim 13, further comprising a circuit board, the first light source and the second light source mechanically coupled to a planar surface of the circuit board.

18. A method for illuminating an object, the method comprising:
    emitting a first beam of light;
    emitting a second beam of light substantially parallel to the first beam of light;
    redirecting the first beam and the second beam such that the beams converge at a selected location; and
    increasing the divergence of at least one of the first beam and the second beam.

* * * * *